United States Patent
Brown et al.

(10) Patent No.: US 6,235,467 B1
(45) Date of Patent: May 22, 2001

(54) METHODS FOR IDENTIFYING CELL CYCLE REGULATORS

(75) Inventors: Susanne M. Brown; Alasdair R. Maclean; June Harland, all of Glasgow (GB)

(73) Assignees: Medical Research Council, London; The University Court of the University of Glasgow, Glasgow, both of (GB)

( * ) Notice: Subject to any disclaimer, the term of this patent is extended or adjusted under 35 U.S.C. 154(b) by 0 days.

(21) Appl. No.: 09/380,760

(22) PCT Filed: Mar. 16, 1998

(86) PCT No.: PCT/GB98/00772

§ 371 Date: Nov. 29, 1999

§ 102(e) Date: Nov. 29, 1999

(87) PCT Pub. No.: WO98/41873

PCT Pub. Date: Sep. 24, 1998

(30) Foreign Application Priority Data

Mar. 14, 1997 (GB) .................................................. 9705299
Sep. 18, 1997 (GB) .................................................. 9719919

(51) Int. Cl.[7] .................................................... C12Q 1/70
(52) U.S. Cl. ................................. 435/5; 435/7.1; 435/7.21
(58) Field of Search ................................. 435/7.21, 4, 15, 435/5, 7.1; 436/516

(56) References Cited

U.S. PATENT DOCUMENTS 5,834,216 * 11/1998 Roizman et al. .................. 435/7.21

FOREIGN PATENT DOCUMENTS

| WO 96 14334 | 5/1996 | (WO) . |
| WO 96 35715 | 11/1996 | (WO) . |
| WO 97 10349 | 3/1997 | (WO) . |
| WO 96 04726 | 2/1998 | (WO) . |

* cited by examiner

Primary Examiner—Donna C. Wortman
Assistant Examiner—Robert A. Zeman
(74) Attorney, Agent, or Firm—Nixon & Vanderhye PC

(57) ABSTRACT

The present invention relates to a method for identifying a substance capable of disrupting an interaction between (i) a herpes simplex virus (HSV) ICP34.5 polypeptide or a homologue thereof, or a derivative thereof, and (ii) proliferating cell nuclear antigen (PCNA) or a homologue thereof, or a derivative thereof. The method comprises: (a) providing an HSV ICP34.5 polypeptide or a homologue thereof, or a derivative thereof, as a first component; (b) providing PCNA, or a homologue thereof, or a derivative thereof, as a second component; (c) contacting the two components with a substance to be tested under conditions that would permit the two components to interact in the absence of the substance; and (d) determining whether the substance disrupts the interaction between the first and second components.

5 Claims, 4 Drawing Sheets

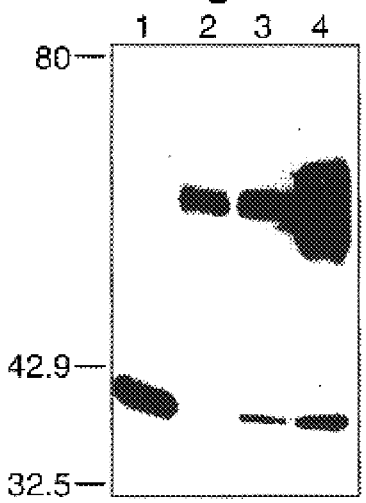
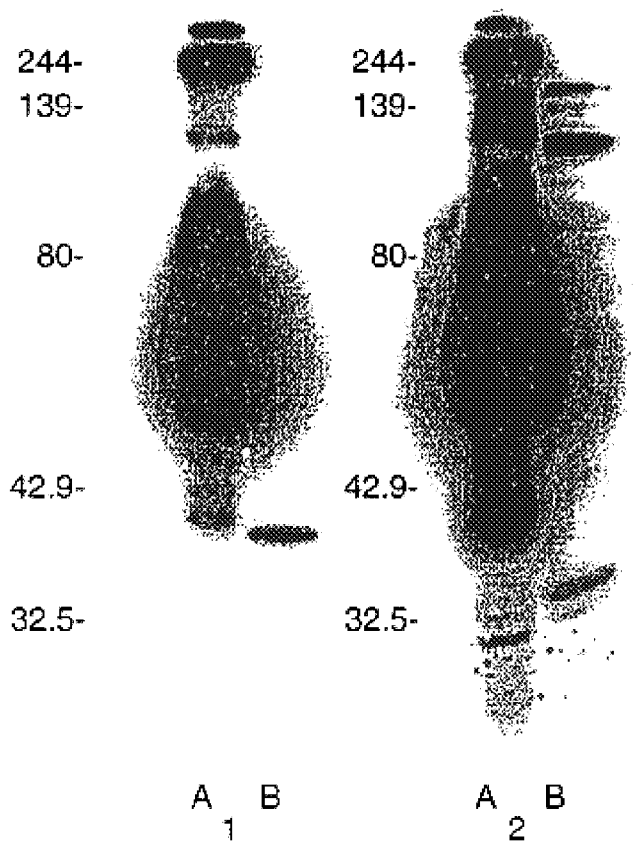

SEQUENCE LISTING

<160> NUMBER OF SEQ ID NOS: 3

<210> SEQ ID NO: 1
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 1
gctgagaaag tcacagtcca t                                          21

<210> SEQ ID NO: 2
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 2
ccatgctctg gccctggaat c                                          21

```
<210> SEQ ID NO: 3
<211> LENGTH: 36
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 3
aagcttgaat tcatgaagga tccccctgag aaagtc                              36
```

METHODS FOR IDENTIFYING CELL CYCLE REGULATORS

FIELD OF THE INVENTION

This invention relates to methods for identifying substances capable of regulating the cell cycle. It further relates to the use of said substances in treating or preventing viral infection, cancer or cell death.

BACKGROUND TO THE INVENTION

Herpes simplex virus (HSV) has a virulence determining locus in the long repeat region of its genome (Ackermann et al., 1986; Chou and Roizman, 1990; McGeoch et al., 1991; Dolan et al., 1992). The virulence phenotype has been specifically assigned to the RL1 gene and its encoded protein ICP34.5 (McKie et al., 1994). Null mutants in ICP34.5 are totally avirulent in mice (Taha et al., 1989a, b; Chou et al., 1990; MacLean et al., 1991) and the function of the protein in vitro has been shown to be cell type and cell state specific, depending on the stage in the cell cycle and the differentiation state (Brown et al., 1994).

One ICP34.5 function demonstrated in a human neuroblastoma cell line is the preclusion of host cell protein synthesis shut-off via the protein kinase PKR pathway following HSV infection (Chou and Roizman, 1992; Chou et al., 1995). This response to expression of ICP34.5 is however not ubiquitous and the precise molecular functions of ICP34.5 remain unknown.

A 63 amino acid carboxy terminal domain of ICP34.5 has been shown to share significant homology (McGeoch and Barnett, 1991) with the carboxy domain of the mouse myeloid differentiation protein MyD116 (Lord et al., 1990) and the hamster growth arrest and DNA damage gene GADD34 (Fornace et al., 1989) although the amino terminal parts of the proteins are quite diverse. The role of MyD116 and GADD34 in the cell appears to be in blocking growth and DNA replication following damage and thus they may act as tumour suppressor genes. The HSV type 1 (HSV1) strain 17 ICP34.5 protein comprises 248 amino acids whereas MyD116 and GADD34 are 657 and 590 amino acids respectively. Chou and Roizman (1994) have demonstrated that the carboxy terminus 63 amino acids are essential but not necessarily sufficient for the host cell shut-off phenotype of ICP34.5 and can be replaced by the homologous domain of

SUMMARY OF THE INVENTION

The present invention is based on the finding that ICP34.5 and MyD116 both interact, via their conserved domain, with proliferating cell nuclear antigen (PCNA). PCNA plays a role in several key cellular processes associated with cell cycle control and the maintenance of genome integrity. PCNA is involved in nucleotide excision repair where it associates with replication factor C and DNA polymerase $\epsilon$ to form a component part of the DNA repair complexes. It is also involved in DNA replication where it acts as a processivity factor for eukaryotic DNA polymerase $\delta$. Further, PCNA forms a complex with $p21^{CIP1}$, an inhibitor of cyclin dependent kinases. The levels of p21 are up-regulated by the tumour suppressor p53, which is in turn activated by DNA damage and other forms of cellular stress.

Thus, the findings on which the present invention is based indicate that the role of HSV ICP34.5 may be to prevent host cell shut-down and/or cell death in response to cellular stress induced by viral infection, allowing viral replication to continue. In particular, an interaction between the C-terminus of ICP34.5 and PCNA may prevent or modify the interaction of PCNA with other components of the cell cycle control machinery which would normally result in host cell shut-down and/or cell death. One of these components may be MyD116/GADD34 and their homologues since ICP34.5 shares sequence homology with a region of MyD116/GADD34 and our results demonstrate that both ICP34.5 and MyD116 can bind PCNA.

Several possibilities arise from these findings. It may be possible to prevent viral propagation or the establishment of viral infection by disrupting the interaction between ICP34.5 and PCNA.

Thus the present invention provides a method for identifying a substance capable of disrupting an interaction between (i) a herpes simplex virus ICP34.5 polypeptide or a homologue thereof, or a derivative thereof, and (ii) proliferating cell nuclear antigen (PCNA) or a homologue thereof, or a derivative thereof, which method comprises:
(a) providing an HSV ICP34.5 polypeptide or a homologue thereof, or a derivative thereof, as a first component;
(b) providing PCNA or a homologue thereof, or a derivative thereof, as a second component;
(c) contacting the two components with a substance to be tested under conditions that would permit the two components to bind in the absence of the said substance; and
(d) determining whether the said substance disrupts the interaction between the first and second component.

The method of the invention may further comprise:
($e_1$) administering a said substance which has been determined to disrupt the interaction between the first and second components to a mammalian cell; and
($f_1$) determining the effect of the said substance on the cell cycle of the said cell.

The ability of the substance to induce cell cycle arrest may be determined. The ability of the substance to induce cell death by apoptosis may be determined.

Alternatively, the method of the invention may further comprise:
($e_2$) administering a virus to a cell in the absence of a said substance which has been determined to disrupt the interaction between the first and second components;
($f_2$) administering the virus to the cell in the presence of the said substance; and
($g_2$) determining if the said substance reduces or abolishes the susceptibility of the cell to viral infection.

The invention further provides a substance capable of disrupting an interaction between (i) a herpes simplex virus ICP34.5 polypeptide or a homologue thereof, or a derivative thereof, and (ii) PCNA or a homologue thereof, or a derivative thereof, for use in treating the human or animal body by therapy or for use in diagnosis, whether or not practised on the human or animal body. Such a substance may thus be used in the prevention or treatment of viral infection. Preferably the target virus has homology to a herpes simplex virus. More preferably the target virus is a herpes simplex virus. Preferably the substance is identified by the method of the invention.

Since MyD116 and GADD34 have sequence homology with ICP34.5 and we have shown that MyD116 can bind to PCNA, it is likely that at least some of the activities of MyD116/GADD34 are mediated via similar interactions and pathways to ICP34.5. MyD116/GADD34 are thought to be involved in blocking cell growth and DNA replication following cellular stress, including DNA damage. Furthermore, we have shown that MyD116 is expressed in a range of different cell types of different species and that expression is not dependent on the differentiation state of the cell. Thus MyD116 is likely to have a conserved role in cell cycle regulation.

The invention therefore further provides a substance capable of disrupting between (i) a herpes simplex virus ICP34.5 polypeptide or a homologue thereof, or a derivative thereof, and (ii) PCNA or homologues thereof, or derivatives thereof, for use in regulating the cell cycle of a mammalian cell. Again, preferably the substance is identified by the method of the invention. The substance may be used for inducing growth arrest and/or cell death. In that event, the mammalian cell is typically a tumour cell.

One function of ICP34.5 appears to be to prevent cell death induced by viral infection. This may be achieved by competing with MyD116/GADD34 or their homologues for PCNA. It may therefore be possible to prevent cell death in non-infected cells by inhibiting the activity of MyD116/GADD34 or their homologues. Thus the substance above may alternatively be used for preventing cell death. Preferably the cell is then a cell of the central or peripheral nervous system of a mammal, especially a human.

The invention also provides a method of regulating the cell cycle in a mammalian cell, which method comprises administering to said cell a substance capable of disrupting an interaction between (i) a herpes simplex virus ICP34.5 polypeptide or a homologue thereof, or a derivative thereof, and (ii) PCNA or a homologue thereof, or a derivative thereof.

A further aspect of the invention relates to the identification of a novel human GADD34 homologue. The cellular GADD34 homologue is induced in response to HSV infection in permissive mammalian cells. Thus the invention provides a human GADD34 homologue which has one or more of the following features:

(i) a molecular :mass of approximately 70 kDa as determined by SDS-PAGE;

(ii) a conserved region which is cross-reactive with an anti-ICP34.5 antibody;

(iii) cross-reactive with an anti-GADD34 antibody;

(iv) induced in permissive mammalian cells in response to HSV infection;

(v) not induced in permissive mammalian cells in response to heat shock or UV damage; and (vi) not induced in non-permissive mammalian cells in response to HSV infection.

Preferably, the conserved region of the 70 kDa cellular homologue is at least 70% homologous with the C-terminal conserved region of hamster/human GADD34, more preferably at least 85% homologous. It is also preferred that the conserved region has a similar degree of homology with the C-terminal 63 amino acid residues of an HSV ICP34.5 polypeptide as that exhibited by MyD116/GADD34, preferably at least 30%. The conserved region over which the homology is compared is 30, preferably 50, more preferably 60 amino acids.

The human GADD34 homologue is only induced in response to HSV infection in permissive cells and not in non-permissive cells. Typically, induction of the human GADD34 homologue occurs at about 4 hours post-infection and plateaus at between 12 and 24 hours post-infection. Some HSV strains used therapeutically are attenuated to prevent establishment of a lytic replication cycle in non-permissive cell types and thus reduce their neurovirulence. For example, ICP34.5 negative strains are unable to replicate in fully differentiated, non-dividing neuronal cells.

However, it may be desirable to use the lytic replication cycle of HSV in some therapeutic methods, for example cancer therapy. Thus it will be useful to determine easily whether a cell type is permissive or non-permissive for replication of attenuated HSV strains.

Our results indicate that the induction of the human GADD34 homologue may be used to determine whether a cell type will allow lytic replication by attenuated strains, for example, ICP34.5 negative HSV strains. In particular, it will be useful to determine if a tumour cell type is permissive or non-permissive. If the tumour cell-type is permissive, then it will be possible to administer ICP34.5 null mutants which will still replicate in the tumour cells. Lytic replication of attenuated HSV strains in the tumour cells may improve the tumour killing properties of the HSV strains.

Thus the invention provides a method for determining whether a cell is permissive for HSV lytic replication which method comprises:

(a) infecting said cell with wild-type HSV and (b) determining if the 70 kDa cellular GADD34 homologue is induced.

Typically, induction of the GADD34 homologue is determined by Western blotting cellular extracts. Preferably the cell is a human tumour cell.

DETAILED DESCRIPTION OF THE INVENTION

Polypeptide Components

The first component comprises a ICP34.5 polypeptide or a homologue thereof or a derivative of ICP34.5 or of an ICP34.5 homologue. Homologues of ICP34.5 include MyD116 and GADD34. Derivatives of ICP34.5 include fragments of ICP34.5, MyD116 and GADD34 which comprise at least a region having substantial homology to the C-terminal 63 amino acids of ICP34.5. The fragments may be up to 63, 70, 80, 90 or 100 amino acid residues long. The minimum fragment length may be 6, 10, 20 or 30 amino acid residues. Herein, substantial homology for fragments of ICP34.5 is regarded as a sequence which has at least 70%, e.g. 80%, 90% or 95%, amino acid homology (identity) over 30, preferably 50, more preferably 60 amino acids with the C-terminal 63 amino acids of ICP34.5. Substantial homology for fragments of MyD116 and GADD34 is regarded as a sequence which has a similar degree of homology with the C-terminal 63 amino acid residues of an HSV ICP34.5 polypeptide as that exhibited by MyD116/GADD34, preferably at least 30%. Derivatives further include variants of ICP34.5 and its homologues or derivatives, including naturally occurring allelic variants and synthetic variants which are substantially homologous to said ICP34.5 and its homologues. The sequence of HSV ICP34.5 is described in Chou and Roizman, 1990; Dolan et al., 1992 and McGeoch et al., 1991.

Derivatives of ICP34.5 and its homologues may contain one or more (e.g. 2, 3, 5 or 10) substitutions, deletions or insertions, including conserved substitutions. Conserved substitutions may be made according to the following table which indicates conservative substitutions, where amino acids on the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |
| OTHER | | N Q D E |

Derivatives may be in the form of a fusion protein wherein ICP34.5, a homologue or derivative thereof is fused, using standard cloning techniques, to another polypeptide which may, for example, comprise a DNA-binding domain, a transcriptional activation domain or a ligand suitable for affinity purification (for example glutathione-S-transferase or six consecutive histidine residues).

The second component is selected from PCNA or homologues thereof, and their derivatives. Preferably the PCNA is mammalian PCNA, more preferably human PCNA. Derivatives of PCNA include fragments, preferably comprising at least 30 amino acids, more preferably at least 50 amino acids, which are capable of binding to ICP34.5. Derivatives further include variants of PCNA, its homologues or derivatives, including naturally occurring allelic variants and synthetic variants which are substantially homologous to said PCNA. In this context, substantial homology is regarded as a sequence which has at least 70%, e.g. 80% or 90% amino acid homology (identity) over 30, preferably 50, more preferably 60 amino acids with PCNA.

Derivatives of PCNA and its homologues may contain one or more (e.g. 2, 3, 5 or 10) substitutions, deletions or insertions, including conserved substitutions. Conserved substitutions may be made according to the table represented and described above. Derivatives may be in the form of a fusion protein wherein said PCNA, homologue or derivative thereof is fused to another polypeptide which may, for example, comprise a DNA-binding domain, a transcriptional activation domain or a ligand suitable for affinity purification (for example glutathione-S-transferase or six consecutive histidine residues).

The first and second components used in the assays may be obtained from mammalian or yeast cellular extracts or produced recombinantly from, for example, bacteria, yeast or higher eukaryotic cells including mammalian cell lines and insect cell lines. Preferably, the first and second components used in the assays are recombinant.

Candidate Substances

A substance which disrupts an interaction between the first component (a polypeptide selected from an HSV ICP34.5 polypeptide or a homologue thereof, or a derivative thereof) and the second component (PCNA or its homologues, and derivatives thereof) may do so in several ways. It may directly disrupt the binding of the two components by, for example, binding to one component and masking or altering the site of interaction with the other component. Candidate substances of this type may conveniently be screened by in vitro binding assays as, for example, described below. Examples of candidate substances include non-functional homologues of the first or second components as well as antibodies which recognise the first or second components.

A substance which can bind directly to the first or second component may also inhibit an interaction between the first component and the second component by altering their subcellular localisation thus preventing the two components from coming into contact within the cell. This can be tested in vivo using, for example the in vivo assays described below. The term 'in vivo' is intended to encompass experiments with cells in culture as well as experiments with intact multicellular organisms.

Alternatively, instead of preventing the association of the components directly, the substance may suppress or enhance the biologically available amount of one or both of the components. This may be by inhibiting expression of the component, for example at the level of transcription, transcript stability, translation or post-translational stability. An example of such a substance would be antisense RNA which suppresses the amount of MyD116 mRNA translated into protein.

Suitable candidate substances include peptides, especially of from about 5 to 20 amino acids in size, based on the sequence of the conserved C-terminal domain of ICP34.5/MyD116/GADD34, or variants of such peptides in which one or more residues have been substituted. Peptides from panels of peptides comprising random sequences or sequences which have been varied consistently to provide a maximally diverse panel of peptides may be used.

Suitable candidate substances also include antibody products (for example, monoclonal and polyclonal antibodies, single chain antibodies, chimeric antibodies and CDR-grafted antibodies) which are specific for the first component or the second component, preferably the conserved C-terminal domain of ICP34.5/MyD116/GADD34. Furthermore, combinatorial libraries, peptide and peptide mimetics, defined chemical entities, oligonucleotides, and natural product libraries may be screened for activity as inhibitors of an interaction between the first component and the second component in assays such as those described below. The candidate substances may be used in an initial screen in batches of, for example 10 substances per reaction, and the substances of those batches which show inhibition tested individually. Candidate substances which show activity in in vitro screens such as those described below can then be tested in in vivo systems, such as mammalian cells which will be exposed to the inhibitor and tested for susceptibility to viral infection or apoptosis as appropriate.

Assays

The assays of the invention may be in vitro assays or in vivo assays, for example using an animal model. One type of in vitro assay for identifying substances which disrupt an interaction between the first component and the second component involves:

contacting a first component, which is immobilised on a soild support, with a non-immobilised second component in the absence of a candidate substance;

contacting the first immobilised component with the non-immobilised second component in the presence of a candidate substance; and determining if the candidate substance disrupts the interaction between the first component and the second component.

Alternatively, the second component may be immobilised and first component non-immobilised.

In a preferred assay method, the first component is immobilised on beads such as agarose beads. Typically this is achieved by expressing the component as a GST-fusion protein in bacteria, yeast or higher eukaryotic cell lines and purifying the GST-fusion protein from crude cell extracts using glutathione-agarose beads (Smith and Johnson, 1988). As a control, binding of the second component, which is not a GST-fusion protein, to the immobilised first component is determined in the absence of the candidate substance. The binding of the second component to the immobilised first component is then determined in the presence of the candidate substance. Any inhibitory effect by the candidate substance can then be evaluated. This type of assay is known in the art as a GST pulldown assay.

The candidate substance may be pre-incubated with the first component or with the second component or added to the reaction mixture after pre-incubation of the first component with the second component. In a similar assay, the second component is a GST fusion protein immobilised on glutathione agarose beads and the first component is a not a GST-fusion protein. It is also possible to perform this type of assay using different affinity purification systems for immobilising one of the components, for example Ni-NTA agarose and histidine-tagged components.

Binding of the first component to the second component (and vice-versa) may be determined by a variety of methods well-known in the art. For example, the non-immobilised component may be labelled (with for example, a radioactive label, an epitope tag or an enzyme-antibody conjugate). The effect of a candidate substance on an interaction between the two components can be determined by comparing the amount of label bound in the presence of the candidate substance with the amount of label bound in the absence of candidate substance. A lower amount of label bound in the presence of the candidate substance indicates that the candidate substance is an inhibitor of interactions between the first component and the second component.

Alternatively, binding may be determined by immunological detection techniques. For example, the reaction mixture can be Western blotted and the blot probed with an antibody that detects the non-immobilised component. ELISA techniques may also be used.

Another method contemplated by the invention for identifying a substance that disrupt an interaction between the first component and the second component involves immobilising the first component on a solid support coated (or impregnated with) a fluorescent agent, labelling the second component with a substance capable of exciting the fluorescent agent, contacting the immobilised first component with the labelled second component in the presence and absence of a test compound, detecting light emission by the fluorescent agent, and identifying inhibitory substances as those candidate substances that reduce the emission of light by the fluorescent agent in comparison to the emission of light by the fluorescent agent in the absence of the test compound. Alternatively, the second component may be immobilised and first component labelled in the assay.

Assays for identifying compounds that disrupt an interaction between the first and second component may involve:

(a) transforming or transfecting an appropriate host cell with a DNA construct comprising a reporter gene under the control of a promoter regulated by a transcription factor having a DNA-binding domain and an activating domain;

(b) expressing in the host cell a first hybrid DNA sequence encoding a first fusion of all or part of the first component and the DNA binding domain or the activating domain of the transcription factor; expressing in the host cells a second hybrid DNA sequence encoding all or part of the second component and the DNA binding domain or activating domain of the transcription factor which is not incorporated in the first fusion;

(c) evaluating the effect of a test compound on the interaction between the first component and the second component by detecting binding of the first component to the second component in a particular host cell by measuring the production of reporter gene product in the host cell in the presence or absence of the test compound; and (d) determining whether the presence of the test compound alters the production of the reporter gene product in comparison to the production of the reporter gene product in the absence of the test compound.

The host cell may be a bacterium or other microbial cell. It may be a yeast or mammalian cell. Presently preferred for use in such an assay are a lexA promoter to drive expression of the reporter gene, the lacZ reporter gene, a transcription factor comprising the lexA DNA domain and the GAL4 transactivation domain and yeast host cells.

The candidate substance, i.e. the test compound, may be administered to the cell in several ways. For example, it may be added directly to the cell culture medium or injected into the cell. Alternatively, in the case of polypeptide candidate substances, the cell may be transfected with a nucleic acid construct which directs expression of the polypeptide in the cell. Preferably, the expression of the polypeptide is under the control of a regulatable promoter.

Candidate substances that are identifiable by the method of the invention as disrupting an interaction between a first component and a second component may be tested for their ability to, for example, reduce susceptibility of cells to viral infection or regulate the cell cycle including apoptosis and growth arrest. Such compounds could be used therapeutically to prevent or treat viral infection. They may also be used therapeutically in regulating the cell cycle of a mammalian cell, including preventing cell death in, for example, neuronal cells, or inducing cell death in, for example, neoplastic cells.

Typically, an assay to determine the effect of a candidate substance identifiable by the method of the invention on the susceptibility of cells to viral infection comprises:

(a) administering a virus, for example HSV1, to a cell, for example a BHK21/C13 cell, in the absence of the candidate substance;

(b) administering the virus to the cell in the presence of the candidate substance; and (c) determining if the candidate substance reduces or abolishes the susceptibility of the cell to viral infection.

The candidate substance may be administered before, or concomitant with, the virus to establish if infection is prevented. Alternatively, the candidate substance may be administered subsequent to viral infection to establish if viral infection can be treated using the candidate substance. Administration of candidate substances to cells may be performed as described above.

The assay is typically carried out in vitro but an animal model could be employed instead. The virus is contacted with cells, typically cells in culture. The cells may be cells of a mammalian cell line, in particular mammalian cells susceptible to infection by the virus in the absence of the candidate substance.

Techniques for assaying infectivity of viruses are well-known in the art. As well as using plaque assays, levels of viral infection can be determined by using recombinant viruses which comprise a reporter gene, for example lacZ. The use of a histochemically detectable reporter gene is especially preferred when experiments are performed with animals, for example mice.

Typically, an assay to determine the effect of a candidate substance identifiable by the method of the invention on the regulation of the cell cycle in a mammalian cell comprises:

(a) administering the candidate substance to the cell; and (b) determining the effect of the candidate substance on the cell cycle, including, for example induction of cell cycle arrest and/or cell death by apoptosis.

Administration of candidate substances to cells may be performed as described above. The assay is typically carried out in vitro. The candidate substance is contacted with the cells, typically cells in culture. The cells may be cells of a mammalian cell line.

The ability of a candidate substance to induce apoptosis can be determined by administering a candidate compound to cells and determining if apoptosis is induced in said cells. The induction of apoptosis can be determined by various means. There are several techniques known to a skilled person for determining if cell death is due to apoptosis. Apoptotic cell death is characterised by morphological changes which can be observed by microscopy, for example cytoplasmic blebbing, cell shrinkage, internucleosomal fragmentation and chromatin condensation. DNA cleavage typical of the apoptotic process can be demonstrated using TUNEL and DNA ladder assays.

Alternatively, it may be desired to prevent apoptotic cell death by administering a substance identifiable by the method of the invention which prevents an interaction between MyD116 or GADD34 and their homologues, and PCNA. Several techniques known in the art for inducing apoptosis in cells may be used. For example, apoptosis may be induced by stress including UV exposure, growth factor deprivation and heat shock. The ability of the candidate substance to inhibit such apoptosis may be determined by comparing cells exposed to stress in the presence of the candidate substance with those exposed to stress in the absence of the candidate substance.

In a preferred embodiment of the above-described assays, ICP34.5 and derivatives thereof are used in an experimental system to study normal cellular interactions. For example, derivatives of ICP34.5, including deletion, insertion and substitution mutants, can be used to disrupt an interaction between MyD116 and PCNA. This can be tested in vitro using the in vitro assays described above. The interaction between MyD116 and PCNA can also be disrupted in vivo by introducing ICP34.5 and derivatives thereof, including deletion, insertion and substitution mutants, into cells in vivo, preferably mammalian cells, more preferably human cells. ICP34.5 and its derivatives can be introduced into the cells using techniques described above, for example transfection of nucleic acid constructs encoding ICP34.5 and its derivatives, or using viral vectors, preferably HSV. The effect of this disruption can be determined using immunoprecipitation studies or, alternatively, by analysing the effect on cell cycle control using, for example, the assays and techniques described above. Any in vitro data obtained may be used to assist in the rational design of ICP34.5 derivatives for use in the in vivo studies. In addition, the precise regions/amino acid residues of ICP34.5 which bind to PCNA can determined by in vitro binding studies using ICP34.5 derivatives and PCNA. This will also assist in the rational design of ICP34.5 derivatives for use in the in vivo studies.

Thus ICP34.5 and its derivatives, which are readily distinguished from cellular constituents, may be used as a tool to investigate cell cycle control.

The induction of the 70 kDa cellular homologue of GADD34 in cells by infection with wild-type HSV may be used to determine if a cell is permissive for HSV lytic replication.

A typical assay comprises:

(a) infecting said cell with wild-type HSV and (b) determining if the 70 kDa cellular GADD34 homologue is induced.

Induction of the 70 kDa cellular GADD34 homologue may be determined by, for example, Western blotting cellular extracts. For example, extracts from uninfected cells and cells infected with wild-type HSV are resolved by SDS-PAGE, immunoblotted and probed with an anti-GADD34 antibody, If the homologue has been induced, an approximately 70 kDa cross-reactive band should be present in the infected cell extracts but not the uninfected cell extracts. It is also possible to use extracts of cells infected with an ICP34.5 null HSV mutant as the negative control.

The cells are preferably human tumour cells and are typically obtained from tissue biopsies of patients' tumours.

Therapeutic Uses

An essential part of the HSV infection process appears to be preventing host cell shutdown in response to the infection. We have shown that the mechanism for this may be an interaction between ICP34.5 and components of the cell cycle regulatory apparatus—PCNA. Thus the present invention provides a substance capable of disrupting an interaction between (i) an HSV ICP34.5 polypeptide or a homologue thereof, or a derivative thereof, and (ii) a polypeptide selected from proliferating cell nuclear antigen or homologues thereof, or derivatives thereof, for use in a method of preventing or treating viral infection.

Further, since HSV ICP34.5 and MyD116 appear to be involved in cell cycle regulation through their interaction with PCNA, such a substance may be used to regulate the cell cycle of a mammalian cell. Thus the present invention provides a substance capable of disrupting an interaction between (i) an HSV ICP34.5 polypeptide or a homologue thereof, or a derivative thereof, and (ii) PCNA selected or homologues thereof, or derivatives thereof, for use in a method of regulating the mammalian cell cycle. Typically, said substance may be used to induce cell death, for example in a tumour cell, or to prevent cell death, in for example a cell of the central or peripheral nervous system.

The formulation of a substance according to the invention will depend upon the nature of the substance identified but typically a substance may be formulated for clinical use with a pharmaceutically acceptable carrier or diluent. For example it may formulated for topical, parenteral, intravenous, intramuscular, subcutaneous, intraocular or transdermal administration. A physician will be able to determine the required route of administration for any particular patient and condition.

Preferably, the substance is used in an injectable form. It may therefore be mixed with any vehicle which is pharmaceutically acceptable for an injectable formulation, preferably for a direct injection at the site to be treated. The pharmaceutically carrier or diluent may be, for example, sterile or isotonic solutions. It is also preferred to formulate that substance in an orally active form. Typically, said substance may be a polypeptide, an antibody or a nucleic acid construct. Nucleic acid constructs may be administered by various well-known techniques including lipofection, biolistic transformation or the use of viral vectors.

The dose of substance used may be adjusted according to various parameters, especially according to the substance used, the age, weight and condition of the patient to be treated, the mode of administration used and the required clinical regimen. A physician will be able to determine the required route of administration and dosage for any particular patient and condition.

The invention will be described with reference to the following Example which is intended to be illustrative only and not limiting. In the accompanying drawings:

A solid square marks the position of ICP34.5 of HSV1 strain 17 and an open square that of HSV1 strain F. The arrow marks the position of the HSV induced 70 kDa band. Molecular weight markers are shown on the right hand side in kDa.

Figure 5:
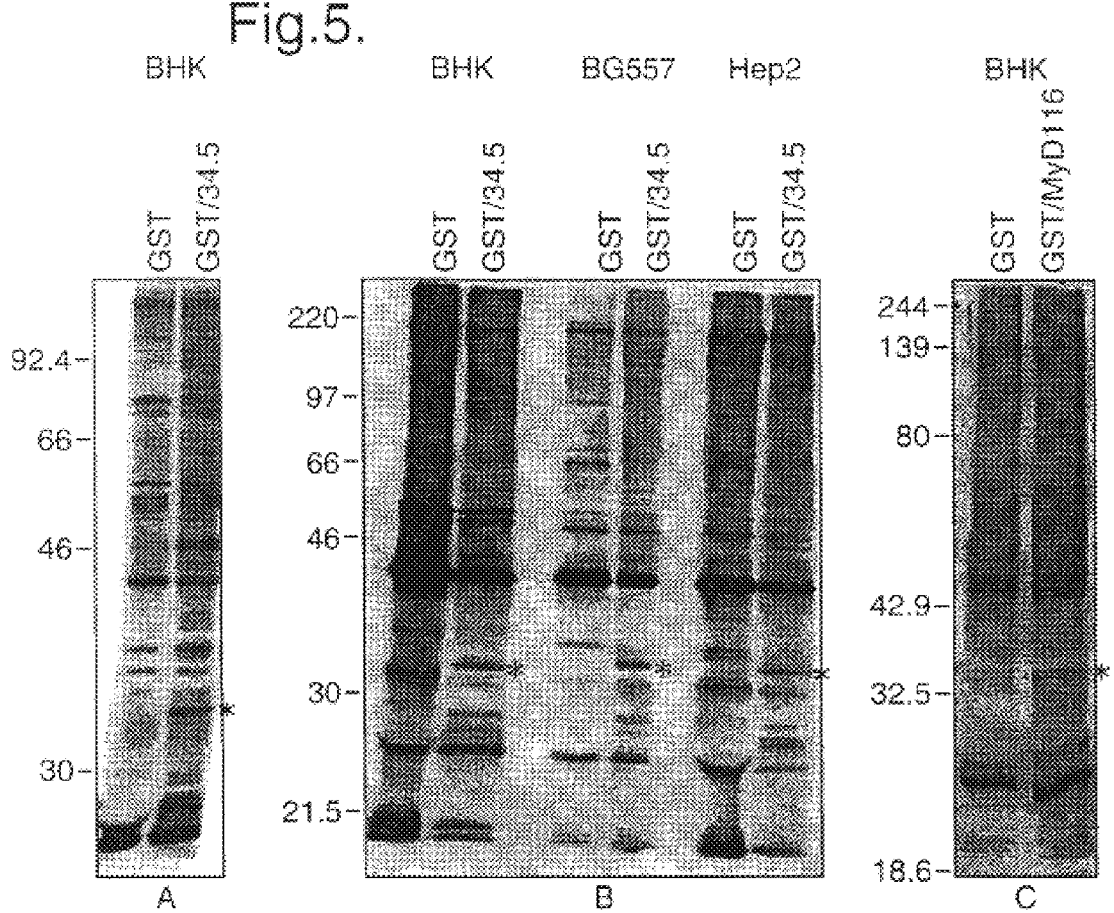

FIG. 5 is a $^{35}$S-methionine profile of GST pull down experiments. (A) BHK21/C13 cell extract pulled down by GST (lane 1) and GST/ICP34.5 (lane 2). (B) BHKL21/C13 cell extract pulled down by GST (lane 1) and GST ICP34.5 (lane 2). BG557 cell extract pulled down by GST (lane 3) and GST/ICP34.5 (lane 4). Hep2 cell extract pulled down by GST (lane 5) and GST/ICP34.5 (lane 6). (C) BHK21/C13 cell extract pulled down by GST (lane 1) and GST/MyD116 (lane 2). The position of the 36 kDa pull down protein is indicated by an asterisk. Molecular weight markers are shown on the left hand side in kDa.

Figure 6:
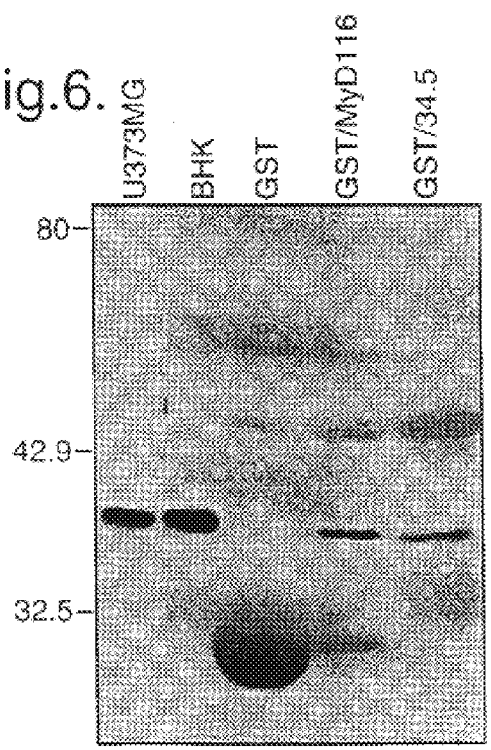

FIG. 6 is a Western blot of a GST pull down experiment using an anti PCNA antibody. Lanes 1, 2 control cell extracts to identify PCNA; lanes 3–5 pull down proteins. U373MG cell extract (lane 1); BHK21/C13 cell extract (lane 2); BHK21/C13 cell extract pulled down by GST (lane 3), BHK cell extract pulled down by GST/MyD116 (lane 4) and by GST/ICP34.5 (lane 5). Molecular weight markers are shown on the left hand side in kDa.

FIG. 7 is a Western blot of 3T6 cell extracts using the PCNA antibody. Whole cell extract (lane 1); an immune precipitate of non specific mouse IgG (lane 2); an immune precipitate with anti PCNA serum (lane 3) and MyD116 serum (lane 4). Molecular weight markers are indicated on the left hand side.

FIG. 8 is a Western blot of an immunoprecipitation performed by adding in vitro transcribed/translated ICP34.5 (Lanes A1 and B1) to BHK cells and immunoprecipitating protein complexes with anti ICP34.5 antibodies. Interacting proteins (Lanes A2 and B2) were separated on SDS PAGE and Western blotted with either anti ICP34.5 (A) or anti PCNA (B) sera. In lane A2 ICP34.5 is detected using anti ICP34.5 serum and in lane B2 using anti PCNA serum PCNA protein is detected. Molecular weight markers are shown on the left hand side in kDa.

EXAMPLE

Materials and Methods

Cells

The following cell lines were used in this study: Baby hamster kidney clone 13 cells (BHK-21(C13); MacPherson and Stoker, 1962); Mouse embryo fibroblasts (3T6); Mouse embryo fibroblasts (3T3); Mouse myeloblast M1 cells (Lord et al., 1990) which were induced to differentiate with the addition of 10 pg/ml of interleukin 6 (IL6) for various lengths of time. The human glioblastoma multiforme cell line U373 (European Tissue Culture Collection), primary human anaplastic astrocytoma cells, BG557 (McKie et al., 1996), the SK-N-SH human neuroblastoma line (American Type Culture Collection) and Hep-2 cells were also used.

Viruses

The parental HSV1 strain 17+ (Brown et al., 1973) and the RL1(ICP34.5) null mutant 1716 (MacLean et al., 1991) were used throughout. HSV1 strain F was also used in some experiments. The HSV2 parental strain HG52 (Timbury, 1971) and the ICP34.5 negative mutant 2604 (Harland and Brown, 1985) were also used.

Virus Growth Properties in vitro

Undifferentiated and differentiated M1 cells were pelleted by centrifugation and 2×10$^6$ cells infected at a multiplicity of infection (MOI) of 5 pfu/cell. After one hour the non-adsorbed virus was washed off, the cells resuspended in 2 ml of growth medium and a single cycle growth experiment carried out.

Northern Blotting

Total cellular RNA was prepared essentially as described by Chomczynski and Sacchi (1987). The poly(A)+ fraction was isolated using the poly(A) Tract mRNA isolation system (Promega) in accordance with the manufacturer's recommended instructions. 2 µg of each poly(A)+ RNA species was separated on a 1% agarose formaldehyde gel. The gel was transferred to a nylon membrane and hybridised overnight to strand-specific riboprobes (Promega) or a random-primed DNA probe. Hybridisations were carried out at 65° C. and 42° C. respectively in 50% formamide; 5×SSPE (1×SSPE contains 0.15 M NaCl, 0.01 M NaH$_2$PO$_4$, and 1 mM EDTA [pH7.4]); 5×Denhardt's solution (1×Denhardt's solution contains 0.1% Ficoll400, 0.1% polyvinylpyrrolidone and 0.1% bovine serum albumin); 0.1% SDS; 100 µg of herring sperm DNA per ml. Filters were washed in 2×SSC (1×SSC contains 150 mM NaCl, 15 mM citric acid); 0.1% SDS (30 mins, RT), 1×SSC; 0.1% SDS (30 mins, 37° C.) and 0.1×SSC; 0.1% SDS (30 mins, 65° C.) then exposed for autoradiography using Kodak XLS-1 film.

Extraction of RNA from Tissues and Cultured Cells

Mouse footpads (skin and muscle), brain (central nervous system) and the pooled lumbar, sacral and thoracic ganglia (peripheral nervous system) tissue were obtained from four week old Balb/C mice and frozen at ~70° C. The tissue was disrupted using a Dounce homogeniser and RNA extracted exactly as for the tissue culture cells using the method of Chomczynski and Sacchi (1987). Poly A$^+$ plus RNA was purified using Dynabeads (Dynal) as described by the manufacturer.

Reverse Transcription Reactions

Reverse transcription was performed on poly(A)$^+$ RNA using avian myeloblast virus reverse transcriptase (Promega) and random hexanucleotide primers under the recommended conditions and incubating for 10 min at 23° C., 45 min at 42° C. and 10 mins at 95° C.

PCR Reactions

PCRs were carried out using 1 to 5 µl of the RT reaction mix in a 100 µl reaction volume using Vent polymerase (Promega). The samples were initially denatured for 5 mins at 95° C., followed by 30 cycles of (denaturation at 95° C. for 1 min, renaturation at 57° C. for 2 min and extension at 72° C. for 2 mins) followed by a final extension at 72° C. for 7 min before transferring the samples to 4° C. The primers from the MyD116/GADD34 conserved domain were:
1) 5' GCTGAGAAAGTCACAGTCCAT 3' (SEQ ID NO:1)
2) 5' CCATGCTCTGGCCCTGGAATC 3' (SEQ ID NO:2)

Cloning and Sequencing of the PCR Products from 3T6 Cells, Murine Tissue, BHK and Human Cells The PCR products (confluent and dividing 3T6 cells, BHK cells, mouse brain and mouse footpad) were gel purified and inserted into SmaI digested pGEM3Zf(-). Subsequently the pGEM3Zf(-) EcoRI/XbaI fragments containing the cloned PCR fragments were ligated with EcoRI/XbaI cut M13 phage DNA and sequenced using a Sequenase kit (USB).

Expression of Both HSV1 ICP34.5 and MyD116 as GST Fusion Proteins and Generation of Antisera a) HSV1 ICP34.5

HSV1 ICP34.5 was expressed as a fusion protein using the pGEX glutathione S-transferase system (Smith and Johnson, 1988). A 780 bp (approx) NcoI/BamHI fragment comprising the entire coding region of ICP34.5 from the initiating ATG was cloned in frame into the NcoI/BamHI sites of pGEX2TNMCR, a derivative of the vector pGEX2T, containing an in frame NcoI restriction site (Pharmacia, Meredith et al., 1994).

b) MyD116

The previously cloned and sequenced 175 bp PCR fragment from 3T6 cells encoding protein sequences conserved between ICP34.5 and MyD116 was used to generate a GST fusion protein. The PCR fragment which had been cloned into the SmaI site of pGEM3Zf(-) was excised using BamHI/EcoRI in the multiple cloning region and inserted into the BamHI/EcoRI sites of the GST gene fusion vector pGEX 1 (Amrad) to create a fusion in frame with the 3' end of GST.

Both GST fusion proteins were expressed in protease-deficient *E. coli* strain BL21 (Stratagene) and purified as described by Smith and Johnson (1988). Expression of GST/ICP34.5 was confirmed by Western blotting using an available anti-peptide serum (McKay et al., 1993). For production of an antiserum to the entire ICP34.5 protein, the fusion protein was specifically eluted from the beads with reduced glutathione. In the case of the MyD/GST fusion protein only a small proportion bound to glutathione agarose beads and in addition the bound material could not be eluted off the beads.

To purify the fusion protein, protein extracts from induced bacteria were run on acrylamide gels, the acrylamide containing the fusion protein was minced in a Dounce homogeniser, eluted with 50 mM ammonium bicarbonate, pH7.8; 0.1% SDS, dried and washed with 80% acetone.

For each immunogen two New Zealand white rabbits were injected with 1 mg fusion protein in complete Freund's adjuvant followed by 3 boosts in incomplete Freund's adjuvant at 14 day intervals and subsequently bled out.

Cloning of the PCR Product Under the CMV Promoter

17mer oligos were synthesized and annealed to generate a linker with a HindIII overhang at the 3' end and a BamHI overhang at the 5' end and containing an EcoRI site, an ATG initiating methionine and two codons downstream to keep the ATG in frame. The linker was inserted into HindIII/BamHI digested pGEM/MyD116 and the newly created EcoRI fragment was excised and introduced into the EcoRI site of pCMV10 (Stow et al., 1993) just downstream of the CMV immediate early promoter. The plasmid, called pCMV/MyD116 had the following sequence:

AAGCTT GAATTC ATG AAGGATCCCCCT-GAGAAAGTC (SEQ ID NO:3) HindIII EcoRI met BamHI MyD116 conserved region . . . EcoRI Lipofections into BHK21C13 cells of pCMV/MyD116 and pCMV10 were carried out as previously described (Sun et al., 1995).

Protein Gels and Western Blotting

Gels were either fixed, treated with Enhance, dried and autoradiographed or used for Western blotting according to the methods recommended by the supplier. Nitrocellulose filters with immobilised blotted proteins were blocked with 2.5% powdered milk and incubated with antibodies for detection by the Amersham ECL method after incubation with the appropriate horseradish peroxidase conjugated immunoglobulin. GST fusion antibodies were cleaned by running through a column containing glutathione agarose beads bound to GST protein.

The following antisera were used for Western blotting and/or immunofluorescence:

Rabbit polyclonal Ab 34.5/GST(1); rabbit polyclonal Ab MyD116/GST(2); rabbit polyclonal IgG Ab GADD34 (Santa Cruz); mouse monoclonal IgG2a Ab PCNA (Novocastra); Protein A peroxidase (Sigma); goat anti-mouse IgG HRP conjugate (Santa Cruz).

Labelling of Cellular Proteins

Labelling of cells was carried out by removing the growth medium, washing the cells with PBS then adding 100 µCi/ml of $^{35}$S-methionine in Eagle's medium containing one fifth the normal concentration of methionine (15 ml per 140 mm plate). The cells were harvested 7 h later for extract preparation. Cell extracts for GST pull-down experiments were prepared by re-suspending the cells in (1 ml per 140 mm plate) 50 mM HEPES, pH7.5; 50 mM NaCl; 0.1% NP40 and protease inhibitors (Boehringer Mannheim protease inhibitor cocktail tablets at the recommended concentration). The cells were sonicated in a sonibath and the debris pelleted by centrifugation.

Analysis of Cellular Proteins Bound to GST Fusions (Pull-down)

Freshly prepared glutathione agarose beads with bound GST fusion protein (50 µl of a 50% slurry) were mixed with 30 ml of labelled cell protein extract and incubated for 1 hr at 4° C. with continuous mixing. The beads were harvested by brief centrifugation and then washed three times in a buffer containing 50 mM TrisHCl, pH 8.0, 0.5 mM NaCl, 1 mM EDTA, 0.5% NP40 and protease inhibitors (Boehringer Mannheim protease inhibitor cocktail tablets dissolved at the recommended concentration). The beads were mixed with SDS-polyacrylamide gel loading buffer, boiled and analysed by SDS-PAGE (Marsden et al., 1976).

Immunoprecipitation of PCNA/ICP34.5 Complexes from Cellular Extracts Incubated with ICP34.5 Protein (A) A plasmid containing the entire ICP34.5 ORF under the control of a T7 promoter and a similar plasmid containing the PCT-amplified MyD116 conserved region under a SP6 promoter were in vitro transcribed/translated using a Promega TNT system according to the manufacturer's instructions. These protein extracts were independently added to BHK cell extracts harvested in Zweig's buffer and incubated at 37° C. for 1–2 hours. Immunoprecipitations were then carried out using 50 µl of either anti ICP34.5 or anti MyD116 sera as appropriate. Antibody incubation took place for 2 hours at 37° C. and subsequently 50 µl of protein A sepharose beads were added and incubation continued for 1 hour at 4° C. Following extensive washing the antibody/antigen complexes were eluted from the sepharose beads using sample buffer and analysed by SDS PAGE. Western blotting was carried out as described before using ICP34.5, MyD116 and PCNA antisera.

(B) infected and uninfected cells ($3 \times 10^7$) were harvested into 1 ml of the same buffer as used in the cell extractions for the GST pull down experiments. Cell extract (250 µl) was incubated with 10 µl of the appropriate antibody overnight at 4° C. 100 µl of 50% v/v protein A sepharose equilibrated in extraction buffer (0.1M Tris pH 8.0% glycerol: 0.5% NP40 and 0.5% deoxycholic acid sodium salt) was added and mixed end over end for 1 hour at 4° C. The protein A sepharose was washed 4 times in the same buffer used for equilibration. Proteins were eluted with 200 µl of polyacrylamide gel loading buffer. The precipitates (50 µl) were run on 10% SDS PAGE and Wester blotted.

Results

Expression of MyD116 RNA in a Range of Cell Types and Tissue

Figure 1:
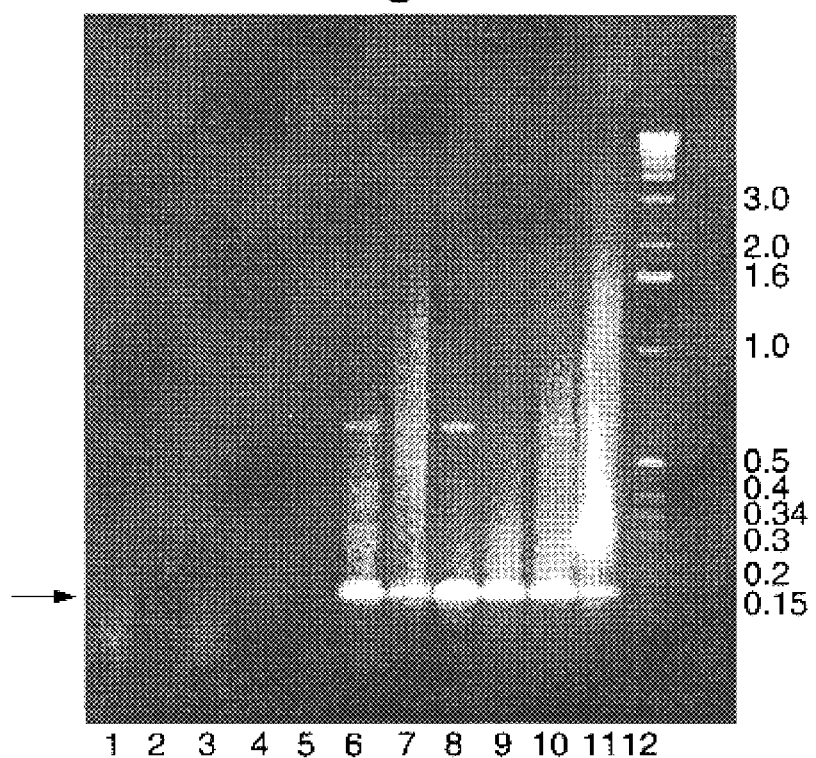
FIG. 1 shows the results of analysis of expression of the MyD116 conserved domain in a range of tissues and cell types. Lanes 1–5: control PCR in the absence of RT: lanes 6–11, RT-PCR. Lanes 1 and 6: confluent 3T6 RNA; lanes 2 and 7: dividing 3T6 RNA; lanes 3 and 8: BHK21/C13 RNA; lanes 4 and 9: mouse brain RNA; lanes 5 and 10: mouse footpad RNA; lane 11: rat dorsal root ganglia RNA; and lane 12: molecular weight markers (kb).

To determine if MyD116 transcripts are ubiquitously expressed, a pair of primers was chosen to amplify the MyD116/ICP34.5 homologous domain of MyD116 and to amplify poly(A)$^+$ RNA from a range of cell types and tissue by RT/PCR. A band of the expected size (175 bp) based on the published sequence of MyD116 (Lord et al., 1990) was detected in both resting and exponentially growing 3T6 cells and BHK21/C13 cells (FIG. 1). In addition this product was detected from brains and footpads of Balb/c mice and from the DRG of rats. Control PCRs in the absence of RT failed to detect a product. We were unable to detect a product from poly(+) RNA extracted from a number of human cells, possibly due to sequence differences affecting the primer homology. The products from the BHK21/C13 and 3T6 cells were cloned into the SmaI site of pGEM3zf(–) and sequenced to confirm that they were homologous to the conserved domain of MyD116. The sequence of both the 3T6 product and the BHK product showed direct homology with the published sequence of MyD116 (Lord et al., 1990). The sequence of rat DRG cDNA previously cloned using the same PCR primers showed 5 separate base pair substitutions leading to altered amino acid sequence.

Pattern of MyD116/GADD34 Expression in M1, BHK and 3T6 Cells

Figure 2:
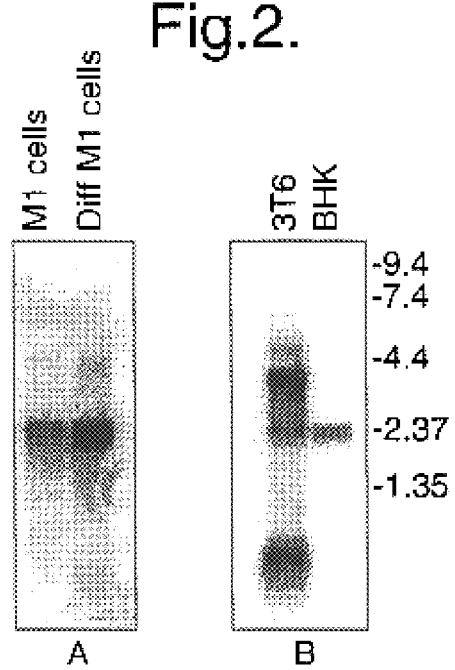
FIG. 2 shows Northern blots of MyD116 RNA in (A) and (B) 3T6 and BHK21/C13 cells. (A) Lane 1: M1 cells; lane 2: differentiated M1 cells. (B) Lane 1: 3T6 cells; lane 2: BHK21/C13 cells. Molecular weight markers are indicated on the right side in kb.

To determine the relative expression of MyD116 in BHK21/C13 and 3T6 cells, poly(A)$^+$ RNA was extracted the cell and Northern blotted using the cloned PCR product as a probe. M1 cells which had previously been shown to be positive for MyD116 (Lord et al., 1990) were used as a control. In M1 cells a band of the expected 2.3 kb size was detected (FIG. 2a). In BHK21/C13 cells a band of 2.3 kb was detected. In 3T6 cells several bands were detected including one of 4 kb which was predominant (FIG. 2) and one of 2.3 kb equivalent to that seen in BHK cells (FIG. 2b). In all cell types there was approximately an equal amount of the cellular β-actin gene (data not shown).

Generation of an Antiserum Against MyD116

To analyse the expression of MyD116 in the various cell types where transcripts had been detected we generated a polyclonal antiserum to the conserved domain of MyD116. The PCR product was cloned into a pGEX vector to generate a GST fusion protein. Following induction with IPTG, the 26 kDa GST band disappeared to be replaced by a 33 kDa band corresponding to the expected size of the fusion protein. Unfortunately only a small proportion of this fusion protein bound to glutathione agarose beads and the bound material could not be eluted off the beads. To purify the fusion protein, protein extracts from induced bacteria were run on acrylamide gels and the fusion protein from sixty gels eluted and pooled. This purified protein was used to immunise two New Zealand white rabbits.

Previous results indicated that expression of MyD116 was dependent on the differentiation state of the cells. Therefore it was essential to have a positive/negative control for the antisera. We constructed a plasmid (pCMV/MyD116) with the MyD116 homologous domain expressed under the control of the HCMV IE promoter. This plasmid was lipofected into BHK21/C13 cells and expression analysed using the generated antisera. On Western blotting a specific band of the expected 7 kDa size was not present in the pCMV/MyD116 lipofected cells compared to control lipofected cells. This was probably due to the low level of lipofection (less than 1% cells based on a control lipofection using a β-galactosidase expressing plasmid and staining for expression). We then assayed expression by immunofluorescence. In pCMV/MyD116 lipofected cells a small percentage of cells (approximately 1%) fluoresced brightly with both anti-MyD116 antiserum (data not shown). No staining was detected in control lipofected cells.

Analysis of MyD116 Expression in M1 Cells

We first analysed the expression of MyD116 in myeloid leukaemic M1 cells before and after induction with IL6 and following an actinomycin block to detect immediate early response proteins. Both before and after differentiation we were able to detect a 72 kDa band corresponding to the expected size of MyD116. The specificity of this band was demonstrated by our ability to block its detection by preincubation of the antiserum with the MyD116/GST fusion protein but not by GST alone or an unrelated GST fusion protein (data not shown).

Expression of Myd116 Related Proteins in BHK2/C13 and 3T6 Cells

Based on the Northern blot data we anticipated that BHK21/C13 cells and 3T6 cells would express MyD116 or related proteins. To analyse the pattern of expression, Western blots were carried out on BHK21/C13, 3T6, human U373MG and M1 cell extracts plus an extract of HSV1 strain 17$^+$ infected BHK cells. In all cell lines tested, polypeptides of 72 kDa and 68 kDa were detected (FIG. 3a, lanes 1 to 4) demonstrating that MyD116 is synthesised in different cell types of diverse species.

Construction of a GST/ICP34.5 Fusion Protein and Generation of Antiserum

A GST/ICP34.5 fusion protein was constructed by cloning into an appropriate pGEX vector the entire ICP34.5 ORF from the initiating ATG in frame with the 3' end of GST. Following induction with IPTG, the 26 kDa GST band disappeared to be replaced by several bands the largest of which corresponded to the expected 65 kDa size of the fusion protein. There were a number of lower Mr products, which were assumed to be the result of proteolytic degradation. All of these proteins bound efficiently to the glutathione agarose beads and were readily eluted with reduced glutathione.

Further proof that the fusion protein was correct was the positive staining of the largest three largest products with an anti-peptide serum raised against the ATP trimer present in ICP34.5 (McKay et al., 1993). The GST protein was used to immunise two New Zealand white rabbits. The antiserum from each of the two rabbits specifically detected ICP34.5, present in 17+ infected extracts but not in 1716 infected extracts, up to a dilution of 1:32,000, a considerably higher affinity than any other available ICP34.5 antiserum. Using the antibody at a dilution of 1:800, the protein was not detectable from 17+ infected extracts beyond a titre of 1:4, confirming our previous conclusions that ICP34.5 is a low abundance protein (data not shown).

Comparison of Proteins Detected by MyD116/GST Ab, ICP34.5/GST Ab and an Antibody to GADD34

Figure 3:
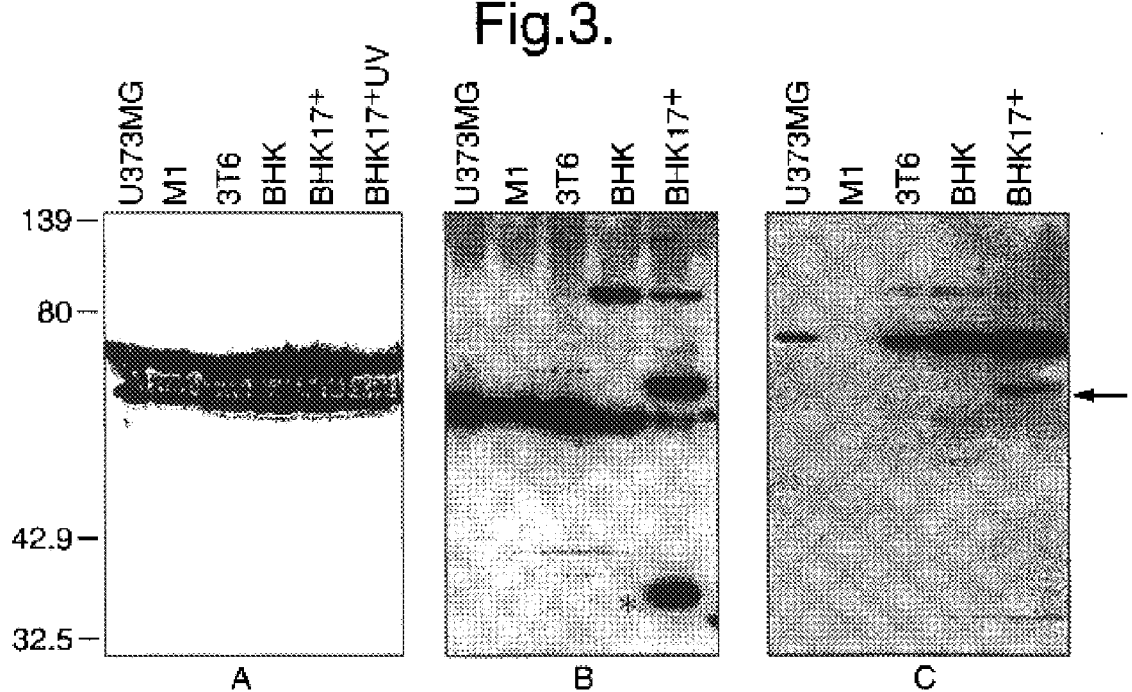
FIG. 3 shows a Western blot against a range of cell types using (A) anti GST/MyD116 serum, (B) anti GST/ICP34.5 serum and (C) anti GADD34 serum. Lane 1: U373MG; lane 2: MI; lane 3: 3T6; lane 4: BHK21/C13; lane 5: HSV1 strain 17 infected BHK21/C13 cell extracts; lane 6: UV inactivated HSV1 strain. The asterisk marks the position of ICP34.5 and the arrow, the position of the HSV induced 70 kDa band, recognised by the anti ICP34.5 and GADD34 sera. Molecular weight markers are shown on the left hand side in kDa.

Using the ICP34.5 fusion protein antibody in Western blotting of infected cell extracts of M1, 3T6, U373 MG and BHK cells plus 17+ infected BHK cell extracts, the antibody clearly detected the 37 kDa ICP34.5 protein (FIG. 3b, lane 5) which is absent in uninfected BHK cells (FIG. 3b, lane 4). In addition, the antibody detected in both uninfected and infected cells a protein of 68 kDa which corresponded to the lower mol. wt species detected by the MyD116/GST antibody (FIG. 3b, lanes 1 to 5 compared with FIG. 3a) which was clearly absent from the uninfected cell extracts.

MyD116 and GADD34 show >80% homology in the 63 amino acid region conserved with ICP34.5. The published literature states that GADD34 is the hamster homologue of the mouse MyD116. To determine if the antibody to MyD116 identified GADD34 and vice versa, Western blots were carried out using U373MG, M1, 3T6, uninfected BHK cell extracts and extracts from BHK cells infected with 17+. In FIG. 3c it can be seen that the proteins identified by the GADD34 antibody are distinguishable by size from those identified by the MyD116 antibody (FIG. 3a). The antibody to GADD34 recognised a 74 kDa species in all the cell extracts, although the amount in the M1 extract was minimal. It also detected a band of 70 kDa in the extract from 17+ infected BHK cells (FIG. 3c, lane 5) which comigrated with the 70 kDa species detected by the antibody to ICP34.5 (FIG. 3b, lane 5). It appears that hamster, human and mouse cells each express MyD116 as well as GADD34.

Figure 4:
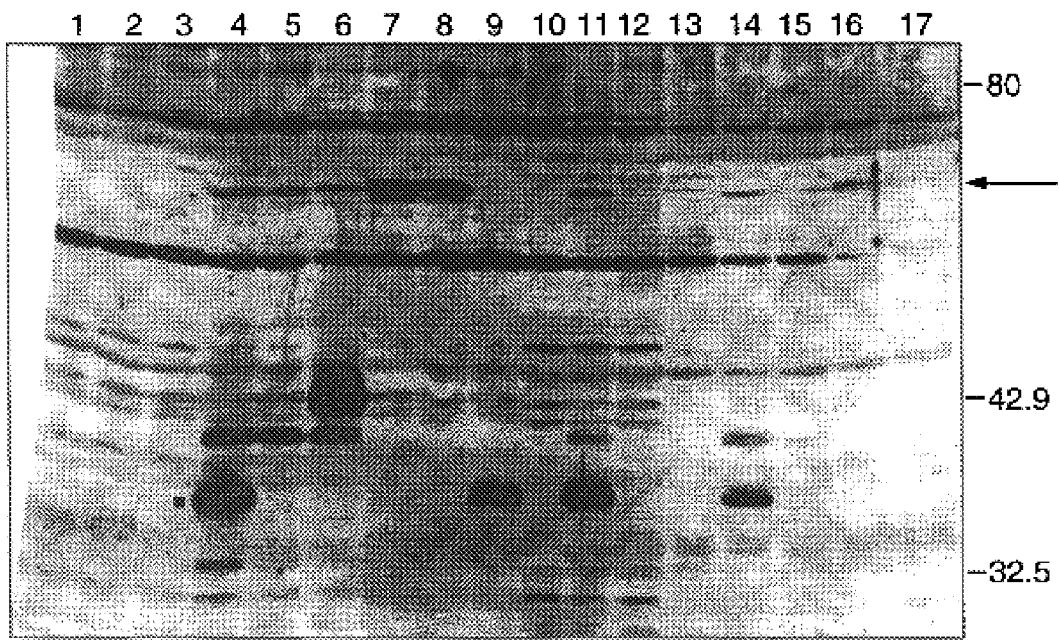
FIG. 4 shows a Western blot using the anti GST/ICP34.5 serum against BHK21/C13 (lanes 1 to 9), 3T6 (lanes 10 to 12) and SK-N-SH (lanes 13 to 17) cell extracts. 42° C., heat shocked cells (lane 1); UV treated cells (lane 2); mock infected (lanes 3, 10, and 13); 17+ infected (lanes 4, 11 and 14); 1716 infected (lanes 5, 12 and 15); F infected (lane 6); HG52 infected (lanes 7 and 16); 2604 infected (lanes 8 and 17); 17+ in the presence of PAA (lane 9).

Correlation of Induction of the Novel 70 kDa Protein with Virus Infection in Different Cell Types To determine the nature of the 70 kDa protein, the following experiments were carried out. Extracts were made from three cell types demonstrating different responses to infection with RL1 negative HSV. These are BHK which are fully permissive, 3T6 which are non permissive due to a block in virus maturation and SK-N-SH which are non permissive due to inhibition of host cell protein synthesis. In BHK cells, the 70 kDa protein was not detected in the absenceof virus infection (FIG. 4, lane 3) or when the cells were stressed either with heat shock (lane 1) or subjected to UV light (lane 2). However the 70 kDa protein was detected following infection with HSV 1 strains 17+ and F (lanes 4 and 6) and with HSV2 strain HG52 (lane 7). In addition, the 70 kDa protein was detected in extracts from cells infected with the HSV1 strain 17+ RL1 mutant 1716 (lane 5) and the HSV2 strain HG52 RL1 mutant 2604 (lane 8).

To determine whether a productive infection was required for induction of this cellular protein, a number of experiments were carried out. In the presence of PAA which blocks viral DNA replication and true late virus gene expression, the 70 kDa protein was not detected (lane 9). Confirmation of the requirement for a productive infection was provided by the absence of induction of theprotein when infection was carried out at the nonpermissive temperature with a ts mutant in IE175 (data not shown).

In 3T6 cells, the 70 kDa protein was not detected in either mock infected (lane 10) or 1716 infected cells (lane 12) but was detected in HSV 1 strain 17 infected cells (lane 11). In SK-N-SH cells, the 70 kDa protein is clearly seen in cells infected with both HSV1 and 2 wild type strains (lanes 14 and 16) but in RL1 negative virus infections (lanes 15 and 17) or mock infected cells (lane 13), there is either no or minimal levels of expression of the novel protein. Most importantly, the level of expression in both mock infected and RL1 infected cells is indistinguishable, demonstrating that the mutant fails to induce the 70 kDa protein. Consistent with the observation that HSV2 strain HG52 has a weaker host cell shut off phenotype (Fenwick and Everett, 1991) than HSV1 strains 17 and F, is the finding that the ,70 kDa induced protein is more strongly expressed following HSV2 (lanes 7, 8 and 16) than HSV1 infection. It is also obvious that a productive infection by HSV1 and not HSV2 induces expression of a 38 kDa protein in all three cell types (lanes 4, 5, 6, 11 and 14).

As expected using the anti ICP34.5 serum, the 37 kDa ICP34.5 protein was detected in HSV1 strain 17+ infected BHK, 3T6 and SK-N-SH cells (lanes 4, 11 and 14, respectively). In the presence of PAA, JSV1 strain 17+ infected BHK cells also express ICP34.5 but at a lower level than when PAA is absent during the infection (lane 9). Strain F of HSV1 induces a 39 kDa, ICP34.5 protein (lane 6) but the type 2 equivalent protein is not recognised by this antiserum.

Analysis of Cellular Proteins Interacting with ICP34.5 and MyD116

To analyse protein interactions with either ICP34.5 or the conserved domain of MyD116, GST pull-down experiments were carried out on $^{35}$S methionine labelled BHK21/C13 cell extracts. In FIG. 5a the results of a pull-down with the GST-ICP34.5 fusion protein can be seen. A strong band of 36 kDa is detected in the GST/ICP34.5 pull-down (lane 2) which is absent in the GST alone control (lane 1). When a similar experiment was carried out using extracts from BG557 and Hep2 cells as well as BHK cells, specific bands of 36 kDa were seen in the GST/ICP34.5 pull-down track in each of the extracts and not in the control GST tracks (FIG. 5b).

The results of a pull-down experiment with the GST/MyD116 fusion protein are shown in FIG. 5c. A band of 36 kDa is present in the GST/MyD116 pull-down and not in the control. Thus there appears to be a 36 kDa cellular protein which specifically interacts with both ICP34.5 and the MyD116 conserved domain.

Identification of Interacting Cellular Proteins

Previous studies had shown that the role of ICP34.5 is cell type and cell state dependent. Therefore proteins involved in growth control and cell cycle regulation may be candidates for interaction with ICP34.5. To identify the interacting proteins we analysed the pulled down proteins by Western blotting using antibodies against proteins involved in growth control and of approximate Mr 36 kDa. One of these antibodies was against proliferating cell nuclear antigen (PCNA), a 36 kDa protein (FIG. 6, lane 5). This monoclonal antibody recognised specifically the 36 kDa protein pulled down by both ICP34.5 and the MyD116 conserved domain (lane 4) confirming the common identity of the interacting protein. Thus both ICP34.5 and the MyD116 conserved domain interact with proteins involved in cell cycle control and progression.

In vivo Complexing of ICP34.5/MyD116 with PCNA

To confirm the biological relevance of the complexing of PCNA with ICP34.5/MyD116, coimmunoprecipitation experiments were carried out on cellular extracts. Firstly it was demonstrated that both PCNA and MyD116 were precipitated by their respective antisera (data not shown).

Thereafter, immunopreciptiation experiments were carried out on uninfected 3T6 cell extracts using the PCNA and MyD116 antisera as well as a non specific antiserum (goat anti mouse). The immunoprecipitated products and non precipitated 3T6 cell extract were run on SDS PAGE and Western blotted with the antiserum to PCNA. A 36 kDa product corresponding to PCNA was detected in the total cell extract (FIG. 7 lane 1) and the immunoprecipitates using the PCNA (lane 3) and the MyD116 (lane 4) antisera. Interestingly, the 36 kDa band was weaker when the precipitation was carried out using the PCNA antibody as opposed to the MyD116 antiserum, indicating that PCNA is only weakly immunoprecipitated by its specific antiserum. No product was detected using the control goat anti mouse serum (lane 2). A 50 kDa band corresponding to the heavy chain of IgG was detected in the immune precipitates, by the protein A HRP (lanes 2 to 4) used in the assay. Similar results were obtained using 17+ and 1716 infected 3T6 cells and mock, 17+ and 1716 infected BHK cells extracts (data not shown).

Unfortunately, ICP34.5 is not precipitated by its antiserum and is also an extremely low abundance infected cell product. Immunoprecipitations on mock, 17+ and 1716 infected BHK cells were carried out using the weakly precipitating PCNA antiserum, run on SDS PAGE and Western blotted by the antisera to both PCNA and ICP34.5. As in the previous experiment, when the PCNA antiserum was used, a 36 kDa band was deleted (data not shown). When the antiserum to ICP35.5 was used to a Western blot, a weak 36 kDa band was seen in 17+ infected but not mock or 1716 infected BHK cells (data not shown, demonstrating that ICP34.5 and PCNA also form a complex within cells.

Immunoprecipitation of PCNA/ICP34.5 Complexes from Cellular Extracts Incubated with ICP34.5 Protein In vitro transcribed/translated ICP34.5 was incubated at 37° C. for 1–2 hours with BHK cell extracts harvested in Zweig's buffer. Immunoprecipitations were then carried out using 50 μl of either anti ICP34.5 or anti MyD116 sera as appropriate. Western blotting was carried out as described before using ICP34.5, MyD116 and PCNA antisera. The results obtained using the anti ICP34.5 sera are shown in FIG. 8. Similar results were obtained using anti MyD116 sera (results not shown).

Discussion

ICP34.5 null mutants of HSV are selectively replication competent both in vivo and in vitro. Following intracerebral inoculation, the mutants display a LD50 value at least $10^6$ fold higher than wild type virus. They replicate inefficiently in peripheral tissue and fail to replicate in DRG neurons but establish latent infections. Stereotactic injection of ICP34.5 negative HSV into xenograft tumours results in replication within the tumour with surrounding tissue excluded. In tissue culture, replication of ICP34.5 negative HSV is cell type and state dependent. In BHK cells, mutant and wild type virus grow equally well. In mouse SK-N-SH cells, the block in replication of ICP34.5 negative virus is due to premature host cell protein synthesis shut-off via the PKR pathway. In mouse embryo fibroblast 3T6 cells, there is a defect in virus maturation but no evidence of premature cell protein synthesis shut-off. In human glioblastoma and anaplastic astrocytoma cells, the mutants range from fully replication competent to totally incompetent.

The ICP34.5 protein has a 63 amino acid carboxy terminal domain which shares significant homology with the mouse myeloid differentiation protein MyD116 and the hamster growth arrest and DNA damage gene GADD34. The conserved domain of the MyD116 gene can substitute for the carboxyl terminus of ICP34.5 to restore the preclusion of host cell protein synthesis shut-off phenotype in SK-N-SH cells but not the in vitro function of ICP34.5. HSV may have evolved by adopting the cellular sequence to guarantee survival by escaping from cellular growth arrest following HSV infection. This leads to the question whether expression of MyD116/GADD34 in cells can complement the lack of ICP34.5 expression and thus is the fate of HSV in specific cell types dependent on the expression of either of these cellular homologues? To answer this question, we have analysed MyD116 and GADD34 expression in different tissues and cell types, in the presence and absence of HSV infection. In addition, we have looked for cellular protein(s) which complex specifically with both ICP34.5 and MyD116 indicating that they function via a common pathway.

MyD116 has been described as a myeloid differentiation primary response gene induced by IL6. The gene was originally shown to be transcribed in M1 myeloblastic leukaemia cells and in bone marrow but not in non-myeloid tissue. MyD116 has been further described as the murine homologue of the hamster GADD34 gene and has been shown to be a DNA damage induced growth arrest gene. We have shown now that MyD116 is transcribed in non-myeloid CNS and PNS tissues and in mouse, hamster and human cells. Sequence analysis of the conserved region derived from cDNAs generated from both 3T6 and BHK cell polyA$^+$ RNA demonstrates complete homology to MyD116. In Northern blot experiments, using the conserved region as a probe, a 2.3 kb transcript was detected from polyA$^+$ RNA of M1 cells with IL6 treatment of the cells resulting in an up regulation of this transcript. An equivalent sized band was detected in both BHK and 3T6 cells. In addition in 3T6 cells, two additional transcripts of 0.6 and 4.0 kb were detected, indicating expression of a family of related genes or alternatively spliced products.

To our knowledge, the MyD116 protein has not been previously identified. The conserved part of MyD116 was expressed as a GST fusion protein and used to produce a polyclonal antiserum. In M1 cells, the antiserum recognised two proteins, a predominant one of 72 kDa, a size compatible with the 675 amino acids predicted from the published sequence and a second one of 68 kDa. The relationship between these two proteins has not yet been determined but may indicate one of the following—alternative start sites using downstream ATGs, alternative splicing or processing. Both proteins were present in M1 cell extracts both before and after differentiation. The specificity of the antiserum was confirmed by blocking with the MyD116/GST fusion protein. As expected from the Northern blot data, the proteins were also detected in hamster BHK cells and mouse 3T6 cells. In addition, we also detected the MyD116 products in human U373MG tumour cells. It is clear from these results that MyD116 is synthesised in different cell types, in different differentiation states and in diverse species. Our data therefore contradict the conclusion that MyD116 is exclusively expressed in myeloid tissues of mice.

MyD116 and GADD34 share more than 80% homology in the 63 amino acid region conserved with ICP34.5. It was possible therefore that the proteins detected by the MyD116 antiserum to GADD34 in Western blotting, when a protein of 74 kDa was detected which is distinguishable from both proteins identified by the MyD116 antiserum. The GADD34 protein was identified in hamster, mouse and human cells although the abundance in the M1 cells was lower than in the other cell types. These findings demonstrate that both MyD116 and GADD34 can be expressed in the same cells and their expression is neither cell type nor species dependent.

The rabbit polyclonal antibody obtained following immunisation with the GST/ICP34.5 fusion protein detected ICP34.5 at an antiserum dilution of 1:32,000, a significantly higher affinity than any other available antibody. The antibody clearly detected ICP34.5 from both HSV1 strain 17 and strain F infected BHK cell extracts with the protein being absent in 1716 infected extracts. It failed to detect ICP34.5 HSV2 strain HG52 and as yet ICP34.5 has not been detected in any HSV2 strain. Of particular interest is the finding that the antibody to ICP34.5 also detected the MyD116, 68 kDa Mr species and identified a novel band of 70 kDa which was present in HSV infected but not uninfected BHK cells. In addition this 70 kDa band was detected by an unrelated antiserum to ICP34.5 (unpublished observations).

As there is no evidence from the sequence analysis of HSV1 strain 17 that the antiserum to ICP34.5 should identify a viral protein other than ICP34.5, it seemed likely that this 70 kDa product was a cellular protein induced upon infection with HSV. In addition this 70 kDa band was detected by an unrelated antiserum to ICP34.5 (unpublished observations). The band was detected in BHK cells infected with HSV 1 and 2; with ICP34.5 null mutants of both stereotypes (demonstrating that it was not an alternatively spliced product from the RL1 gene). The 70 kDa protein was never seen in uninfected BHK cells and stressing the cells either by UV damage or by heat shock failed induce it, indicating that it was expected as a specific response to infection with HSV as opposed to the result of a non-specific insult to the cells.

Experiments using extracts from 3T6 and SK-N-SH cells and BHK cells in which virus replication was blocked with PAA demonstrated that induction of the 70 kDa protein was only seen following a permissive HSV infection. The antibody to GADD34 as well as detecting the 74 kDa, GADD34 protein also weakly detects the 70 kDa protein detected by the antibody to ICP34.5. As (1) the antibody to GADD34 is raised against an epitope from the conserved region and (2) the only part of ICP34.5 and GADD34 which is conserved is the 63 amino acid region, it is highly likely that the 70 kDa species also contains this motif. Like the 74 kDa GADD34 product, the 70 kDa species is not detected by the antibody directed against the conserved domain of MyD116, suggesting homology to GADD34 rather than to My D116.

We conclude that (1) in BHK cells following HSV infection, a 70 kDa protein recognised by both GADD34 and ICP34.5 antisera is induced. It's induction is dependent on productive virus infection and is independent of expression of ICP34.5. The phenotype of ICP34.5 null virus in BHK cells is indistinguishable from wild type, suggesting that the induced cellular protein either allows virus replication to proceed or is a consequence of virus replication. (2) in non-permissive 3T6 and SK-N-SH cells, the novel protein is only induced following wild type HSV infection and not by ICP34.5 negative virus, substantiating the conclusion that it is only induced when a productive infection occurs. The 70 kDa species being a cellular protein, the induced protein is of identical size following infection by several strains of both HSV1 and HSV2 (data not shown). In additional, the level of expression of the 70 kDa protein in cells infected with wild type HSV2 strain HG52 is consistently greater than that expressed following HSV2 strain G or HSV1 strain 17 infection possibly because the virion host shut-off (vhs) function of strain HG52 is highly inefficient compared to that of strains G and 17 (Fenwick and Everett, 1990). The 38 kDa protein recognised by the antiserum to ICP34.5 follows the same pattern of expression as the 70 kDa protein but is only present in HSV1 and not HSV2 infected cells. Experiments are in progress to determine the native of both the 70 kDa and the 38 kDa proteins.

The role of ICP34.5 in HSV replication must be dependent on the expression of one or more cellular proteins which interact either synergistically or antagonistically with ICP34.5 with the possible involvement of other viral proteins. As we have now shown that the expression of a homologous cellular protein is relevant to the ability of cells to support replication of ICP34.5 negative HSV, it became important to identify proteins which not only complexed with ICP34.5 but which complexed with the MyD116/GADD34 family of proteins through their conserved domain.

Our initial approach to identifying complexing proteins has been to carry out GST pull down experiments. When pull downs using BHK extracts with the GST/ICP34.5 fusion protein were compared to the parental GST protein, a number of proteins bound specifically to the fusion protein with the predominant one being 36 kDa. A protein of the same size also complexed when extracts of mouse 3T6, human BG557 and Hep 2 cells were used in the assay. When the GST/MyD116 fusion protein was used in a similar pull down experiment with BHK. extracts, again a predominant band of 36 kDa was clearly identified. These results suggested that both ICP34.5 and MyD116 complexed with the same cellular protein. As the MyD116 fusion protein only had the conserved domain, the complexing must be through this motif.

It has been clear for some time that the requirement for ICP34.5 is dependent on the cell type, stage in the cell cycle and the differentiation state of the infected cells. It seemed likely therefore that proteins involved in cell cycle regulation and growth control could be candidates for interaction with ICP34.5. Analysis of the pull down proteins by Western blotting using a number of antibodies against growth control and cell cycle proteins of approximate Mr 36 kDa showed that an antibody to PCNA specifically recognised the protein interacting with both IPC34.5 and MyD116. The fact that in vitro both the viral and cellular proteins complex with PCNA provides strong evidence for the importance of this interaction.

The GADD34, MyD116, GADD45, MyD118, GADD153 and mdm2 genes have multiple properties in common such as roles in growth control, unusual charge characteristics and similar patterns of expression and regulation. It has been suggested that they participate in a variety of growth control responses with the MyD response dealing primarily with triggering differentiation processes while the GADD responses primarily involve apoptosis: however GADDs must be involved in other pathways as they are induced by treatments which do not affect cell viability. GADD45 and p21 both directly complex and interact with PCNA in competition with each other. The site of interaction between p21 and PCNA has been defined by use of small peptides to inhibit DNA replication. The functions of PCNA, although still being elucidated, include acting as a processivity factor for DNA polymerase gamma and the recruitment of replication factors to DNA replication initiation sites. The interaction of p21 and PCNA blocks the ability of PCNA to support SV40 DNA replication in vitro without apparently interfering with the repair activity of PCNA. It is clear therefore that there are complex interactions between the various proteins involved in cell cycle checkpoints, differentiation, apoptosis, necrosis and tumour suppression. Our findings add to the list of proteins which complex with PCNA and it must be deduced that as GADD34 and GADD45 do not share homology in the 63 amino acid conserved domain, the site of interaction of GADD34 with PCNA is different to that involved in the GADD45 complexing. The effect of this interaction on the other protein complexes involving PCNA is unknown but of obvious interest in elucidating the roles of ICP34.5 and GADD34.

From our findings it can be deduced that following HSV infection ICP34.5 complexes with PCNA either directly or indirectly and this complex allows cellular DNA replication to continue. When ICP34.5 is not present, the PCNA complexing does not take place and the cell goes into a growth arrest state (induced by the insult of virus infection) and does not provide sufficient machinery for the virus to go through the replication cycle.

In some cell types and in some cell states, a GADD34 homologue which can replace ICP34.5, is induced by HSV infection and therefore ICP34.5 is no longer necessary—the assumption being that the GADD34 homologue can substitute for ICP34.5 in complexing with PCNA. It is also clear that MyD116 is expressed in a variety of cells which are both permissive and non-permissive for ICP34.5 null mutants thus MyD116 cannot take the place of the GADD34 homologue, pointing to diverse roles for MyD116 and the GADD34 family of proteins.

References

Ackerman et al, J. Virol. 58, 843–850 (1986).
Bravo et al, Nature , 326, 515–517 (1987).
Brown et al, J. Gen. Virol. 18, 329–346 (1973).
Brown et al, J. Gen. Virol. 75, 2367–2377 (1994a).
Brown et al, J. Gen. Virol. 75, 3679–3686 (1994b).
Chen et al, Oncogene L 11, 1931–1937 (1995).
Chomczynski and Sacchi, Analytical Biochemistry 162, 156–159 (1987).
Chou and Roizman, J. Virol. 57, 629–637 (1986).
Chou and Roizman, Proc. Natl. Acad. Sci. 89, 3266–3270 (1992).
Chou and Roizman, Proc. Natl. Acad. Sci. USA 91, 5247–5251 (1994).
Chou et al, Science 250, 1262–1266 (1990).
Chou et al, Proc. Natl. Acad. Sci. USA 92, 10516–10520, (1995).
Dolan et al, J. Gen. Virol. 73., 971–973, (1992).
Fenwick and Everett, J. Gen. Virol. 71, 2961–2967 (1990).
Flores-Rozas et al, Proc. Natl. Acad. Sci. USA 91, 8655–8659 (1994).
Fornace et al, Mol. Cell. Biol. 9, 4196–4203 (1989).
Harland and Brown, J. Gen. Virol. 66, 1305–1321 (1985).
He et al, J. Virol. 70, 84–90 (1996).
Kesari et al, Lab. Invest., 73, 636–648 (1995).
Kesari et al, J. Neuroscience 16, 5644–5653 (1996).
Kill et al, J. Cell. Sci. 100, 869–876 (1991).
Li et al, Nature 371, 534–537 (1994).
Lord et al, Nucleic Acids Research 18, 2823 (1990).
MacLean et al, J. Gen. Virol. 72, 631–639 (1991).
MacPherson and Stoker, Virology 16, 147–151 (1962).
Marsden et al, J. Gen. Virol. 31, 347–372 (1976).
Maniatis et al, Molecular Cloning; A Laboratory Manual (1982).
McGeoch and Barnett, Nature 353, 609 (1991).
McKay et al, J. Gen. Virol. 74, 2493–2497 (1993).
McKie et al, J. Gen. Virol. 75, 733–741 (1994).
McKie et al, Brit. J. Cancer 74, 745–752 (1996).
Meredith et al, Virology 200, 457–469 (1994).
Prelich et al, Nature 326, 517–520 (1987).
Randazzo et al, Virology 211, 94–101 (1995).
Robertson et al, J. Gen. Virol. 73, 967–970 (1992).
Shivji et al, Cell 69, 367–374 (1992).
Smith and Johnson, Gene 67, 31–40 (1988).
Spivack et al, J. Gen. Virol. 76, 321–332 (1995).
Stow et al, Virology 196, 413–418 (1993).
Sun et al, J. Gen. Virol. 76, 541–550 (1995).
Taha et al, J. Gen. Virol. 70, 705–716 (1989a).
Taha et al, J. Gen. Virol. 70, 3073–3078 (1989b).
Timbury, J. Gen. Virol. 13, 373–376 (1971).
Waga et al, Nature, 369, 574–578 (1994).
Warbrick et al, Current Biology 5, 275–282 (1995).
Zhan et al, Molecular and Cellular Biology 14, 2361–2371 (1994).

What is claimed is:

1. A method for identifying whether a substance inhibits the specific binding between (i) a herpes simplex virus (HSV) ICP34.5 polypeptide, and (ii) proliferating cell nuclear antigen (PCNA), which method comprises:
   (a) providing a first component selected from the group consisting of an HSV ICP34.5 polypeptide, the 63 amino acid C-terminus of ICP34.5, MyD116 and GADD34;
   (b) providing PCNA as a second component;
   (c) contacting the two components with a substance to be tested under conditions that permit the two components to bind in the absence of said substance; and
   (d) determining whether said substance inhibits binding between the first and the second components.

2. The method according to claim 1 further comprising;
   ($e_1$) contacting a substance which has been determined to inhibit binding between the first and the second components with a mammalian cell; and
   ($f_1$) determining the effect of said substance that inhibits binding between said first and said second components on the cell cycle of the said cell.

3. The method according to claim 2 wherein the ability of said substance that inhibits binding between said first and said second components to induce cell cycle arrest is determined.

4. The method according to claim 2 wherein the ability of said substance that inhibits binding between said first and said second components to induce cell death by apoptosis is determined.

5. A method according to claim 1 further comprising:
   ($e_2$) contacting a cell with a virus in the absence of a substance which has been determined to inhibit binding between the first and the second components;
   ($f_2$) contacting the cell with the virus in the presence of said substance that inhibits binding between said first and said second components; and
   ($g_2$) determining whether said substance that inhibits binding between said first and said second components reduces or abolishes the susceptibility of the cell to viral infection.

* * * * *